(12) United States Patent
Nielsen

(10) Patent No.: US 8,036,444 B2
(45) Date of Patent: Oct. 11, 2011

(54) METHOD AND SYSTEM FOR IRRADIATING AND INSPECTING LIQUID-CARRYING CONTAINERS

(75) Inventor: Gert Nielsen, Risskov (DK)

(73) Assignee: InnoScan K/S (DK)

(*) Notice: Subject to any disclaimer, the term of this patent is extended or adjusted under 35 U.S.C. 154(b) by 725 days.

(21) Appl. No.: 12/090,333

(22) PCT Filed: Oct. 15, 2005

(86) PCT No.: PCT/DK2005/000664
§ 371 (c)(1),
(2), (4) Date: Apr. 15, 2008

(87) PCT Pub. No.: WO2007/045235
PCT Pub. Date: Apr. 26, 2007

(65) Prior Publication Data
US 2008/0230720 A1    Sep. 25, 2008

(51) Int. Cl.
*G06K 9/62* (2006.01)
(52) U.S. Cl. .................... 382/142; 250/223 B
(58) Field of Classification Search ............ None
See application file for complete search history.

(56) References Cited

U.S. PATENT DOCUMENTS

| | | | |
|---|---|---|---|
| 2,646,715 A * | 7/1953 | Stout et al. | 356/427 |
| 3,217,877 A | 11/1965 | Honjyo et al. | |
| 3,942,897 A | 3/1976 | Takahashi et al. | |
| 4,615,622 A | 10/1986 | Tagaya et al. | |
| 5,523,560 A * | 6/1996 | Manique et al. | 250/223 B |

FOREIGN PATENT DOCUMENTS

WO    9214142    8/1992

OTHER PUBLICATIONS

International Search Report PCT/DK2005/000664 Dated Jun. 2, 2006.

* cited by examiner

*Primary Examiner* — Brian Werner
(74) *Attorney, Agent, or Firm* — Cantor Colburn LLP

(57) ABSTRACT

A method and system of irradiating a liquid-carrying container for inspection, including rotating the container, its contents or both around a rotation axis and irradiating the container with an electromagnetic radiation beam, wherein the irradiated cross-section of the container, irradiated by the electromagnetic radiation beam, is less than the cross-section of the container; and, a method and system for inspecting a liquid-carrying container for one or more test parameters of the container, the contents of the container, or both, including rotating the container, the contents or both around a rotation axis, irradiating the container with an electromagnetic radiation beam from a first direction along an irradiation center plane substantially parallel to the rotation axis, capturing a representation of a section of the container from a second direction along a detection center plane substantially parallel to the rotation axis, and processing the representation, wherein the irradiated cross-section of the container, irradiated by the electromagnetic radiation beam, is less than the cross-section of the container.

39 Claims, 5 Drawing Sheets

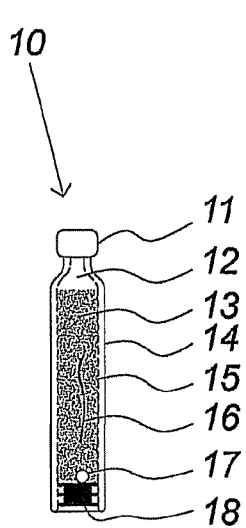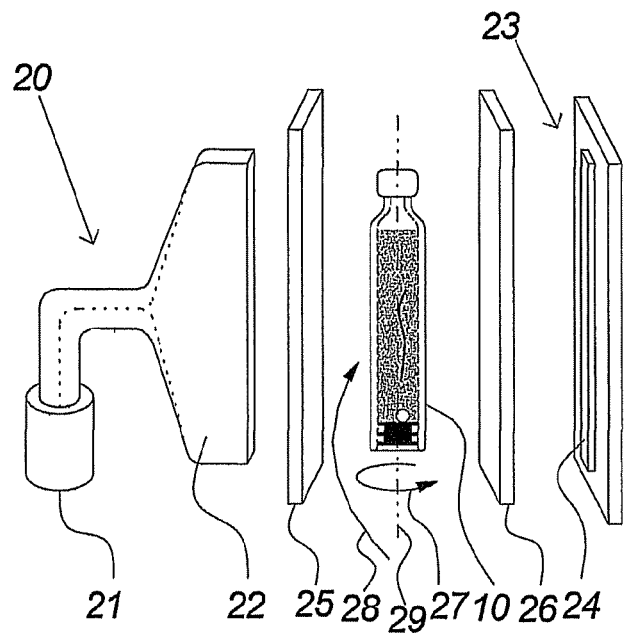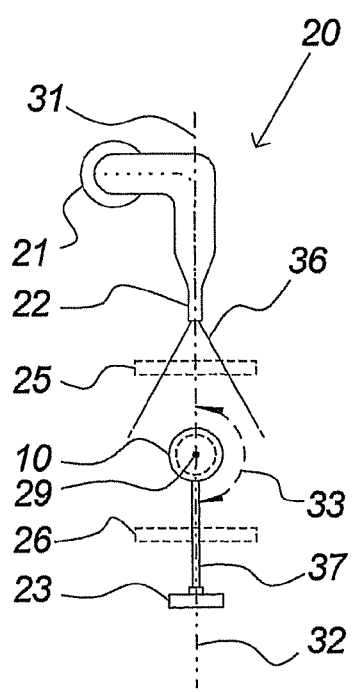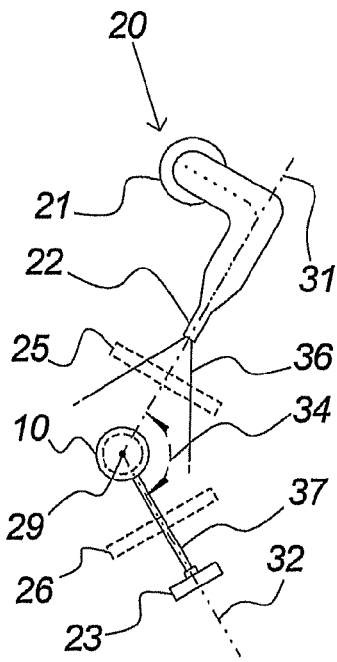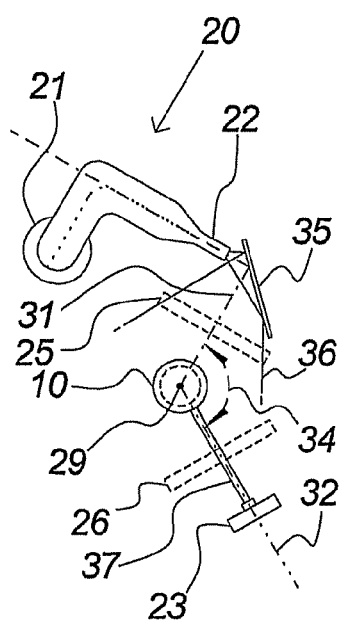

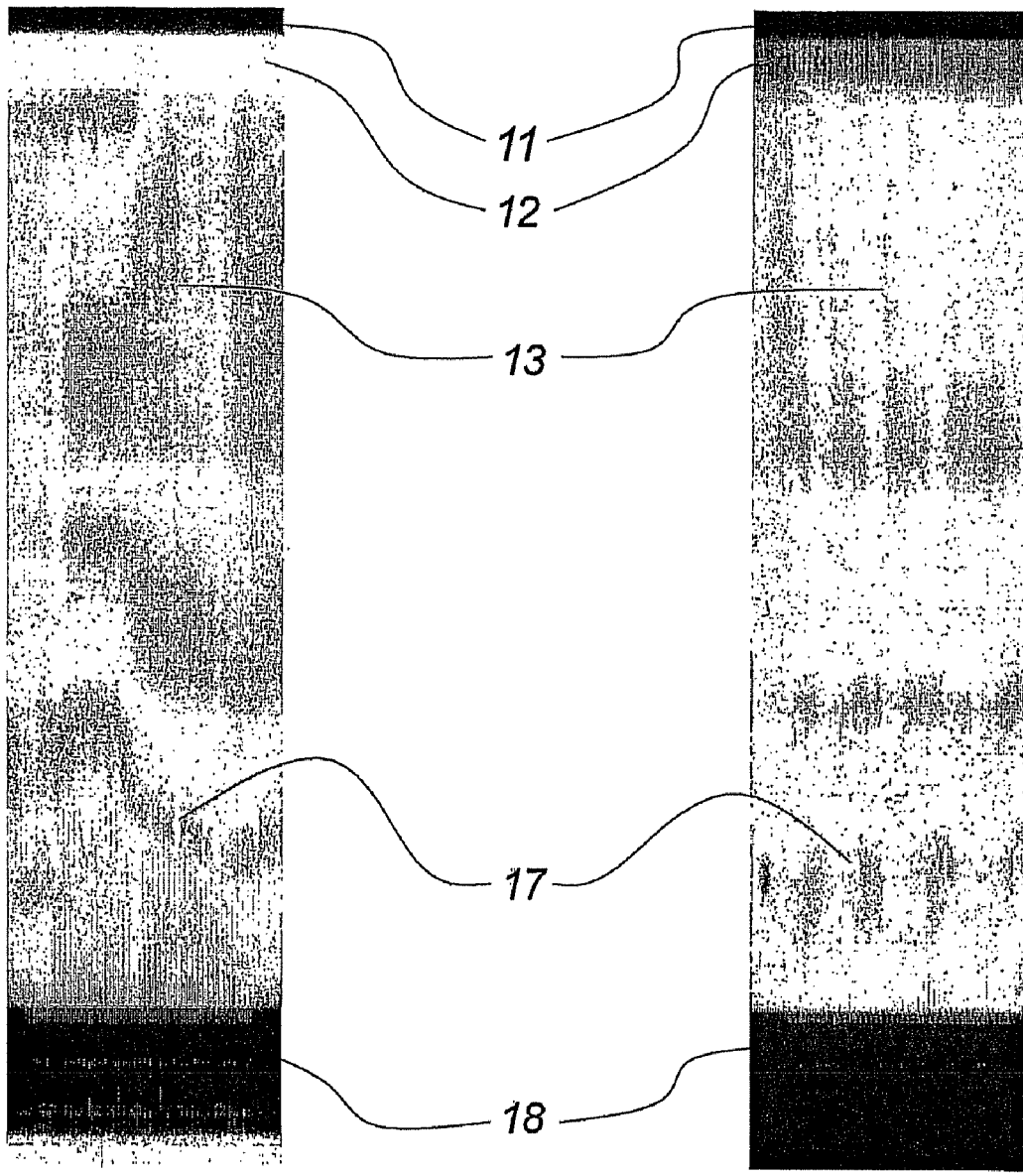
Fig. 9A                    Fig. 9B

METHOD AND SYSTEM FOR IRRADIATING AND INSPECTING LIQUID-CARRYING CONTAINERS

FIELD OF THE INVENTION

The present invention relates to inspection of containers, e.g. containers for pharmaceutical products and their contents, e.g. suspensions, e.g. for quality control purposes.

BACKGROUND OF THE INVENTION

Several methods and apparatuses for inspecting containers and the contents thereof are known in the art. Particularly in the field of manufacture and distribution of medicaments the tolerances regarding the number of contaminated entities or imperfect containers are zero or at least very low. Hence the requirements regarding, e.g., inspection systems for such manufacture processes are high, and there is often a noticeable dependency between the quality of the inspection system, especially its false rejection rate, i.e. the number of flawless entities falsely rejected, and the profit obtainable from the process.

Regarding inspection of substantially transparent liquids contained in transparent containers, several disclosures of particle detection by measuring the amount of light penetrating the container exist. U.S. Pat. No. 3,598,907 and U.S. Pat. No. 3,777,169 thus disclose illuminating a transparent liquid-filled container from beneath, and filming it from the side while the liquid, and any foreign particles, rotate around its vertical axis. The illumination is, however, not very good in the top end of the container opposite to the illumination source, and especially for contents not fully transparent, e.g. suspensions or more or less opaque liquids, the detection rate is low. U.S. Pat. No. 4,095,904, U.S. Pat. No. 4,136,930 and U.S. Pat. No. 4,472,745, and European patent application no. EP 0 293 510 A2, disclose illuminating a transparent liquid-filled container from a direction opposite to the filming or detection direction, i.e. the container is illuminated from behind, and the measured amount of light penetrating the container is used to determined the existence of any foreign particles in the liquid. This method is, however, not optimal, and especially not for contents not fully transparent, e.g. suspensions or more or less opaque liquids, as the liquid or suspension serve as a light diffuser to the illumination, causing the picture of any particle to be so blurred that it may not be detected.

PCT application WO 92/14142 discloses an inspection apparatus where the liquid-filled container is illuminated from an angle between 90 degrees and 180 degrees relative to the direction of detection, and where the detection is made by means of a vertical line scanner. The liquid and any foreign particles therein, rotate around the container's vertical axis, while the container itself is fixed. This inspection apparatus is capable of detecting particles in transparent and, to some degree, more or less opaque liquids, e.g. suspensions. The illumination method of that application has however proved to be non-optimal due to limited optical dynamic range, as, e.g., a suspension acts as an ideal diffuser to the illumination, thereby causing any particle to be very uniformly illuminated and thereby avoids shadows. A particle is thus only detectable if the difference between its colour, e.g. light grey for glass particles and dark grey for opaque particles, and the colour of the diffuse, medium grey background is sufficiently significant.

BRIEF SUMMARY OF THE INVENTION

The invention provides an inspection method and system for containers, in particular containers with opaque or semi-opaque contents, with improved detection rate and reduced false rejection rate.

The invention further provides an improved illumination method and system for use in container inspection apparatuses, in particular for inspection of containers with opaque or semi-opaque contents.

The invention additionally provide an inspection method and system, as well as an irradiation method and system, for containers, in particular containers with transparent contents, with improved detection rate and reduced rejection rate.

The invention relates to a method of irradiating a liquid-carrying container 10 for inspection, comprising rotating said container 10, its contents 12, 13, 16, 17 or both around a rotation axis 29 and irradiating said container 10 with an electromagnetic radiation beam 46, whereby the irradiated cross-section ICS of said container 10, irradiated by said electromagnetic radiation beam 46, is less than the cross-section CS of said container 10.

According to the present invention, an advantageous irradiation method for inspection systems for liquid-carrying containers is provided. According to the present invention the detection rate of such systems may be increased and the false rejection rate decreased by the disclosed irradiation method.

According to the present invention, an irradiation method is provided, which increase the optical dynamic range in digital or analog representations of the inspected container, e.g. images. Thereby the recognition or separation of foreign bodies is significantly improved.

According to a most preferred embodiment of the present invention, the container should not be fully illuminated, i.e. the electromagnetic radiation beam should not irradiate the whole accessible side of the container. Instead only a part of the side of the container should be illuminated, i.e. only a part of the containers cross-section should be illuminated.

According to the present invention, several types of containers may be inspected by means of embodiments of the present invention. The containers are preferably containers for medication or other pharmaceutical product, such as, e.g., ampoules, vials, cartridges, syringes, etc., comprising, e.g., insulin micro-suspensions, but may be of any container type suitable for inspection by electromagnetic radiation and detection.

Further, according to the present invention, the reference to a liquid-carrying container should be understood in a broad sense, i.e. a container at least carrying a liquid or a substance which, as a whole, substantially acts as a liquid under certain conditions, e.g. liquids, suspensions, solutions, emulsions, dispersions, etc. Further, it follows from the nature of the invention that at least some containers may additionally carry items not to be regarded part of the "liquid", e.g. foreign bodies, e.g. glass fragments, and/or required items, e.g. a mixing ball.

According to a preferred embodiment of the present invention, the main body of the container has a cylindrical shape, and the rotation axis is in the centre of that cylinder.

According to the present invention, the electromagnetic radiation beam should comprise a suitable wavelength that does not alter the container or its contents undesirable, and for which a suitable detector exists. The electromagnetic radiation is preferably visible, "white" light, i.e. comprising light of several different wavelengths, but may alternatively be coloured light, infrared light, ultraviolet light, x-rays, microwaves, radio-waves, etc. The electromagnetic radiation beam source may, e.g. comprise a lamp, one or more LEDs, a conventional light bulb, a short arc lamp, a fluorescent tube, a laser beam generator, etc., preferably a tungsten halogen lamp, and possibly light adapting means such as reflectors, filters, lenses, diffusers, etc.

When the width of said irradiated cross-section ICS is less than the width of said cross-section CS of said container 10, preferably less than half the width of said cross-section CS and even more preferably less than a quarter of the width of said cross-section CS, an advantageous embodiment of the present invention has been obtained.

According to a preferred embodiment of the present invention, the electromagnetic radiation beam should be as narrow as possible, preferably less than a quarter of the cross-section, typically the diameter, of the container.

When the width of said irradiated cross-section is less than 10 mm, more preferably less than 6 mm and even more preferably less than 1 mm, an advantageous embodiment of the present invention has been obtained.

According to a preferred embodiment of the present invention, the electromagnetic radiation beam should be as narrow as possible, preferably less than 1 mm.

When said electromagnetic radiation beam 46 comprises visible light, an advantageous embodiment of the present invention has been obtained.

According to a preferred embodiment of the present invention, the container should be illuminated with visible light. Thereby the range of suitable light sources as well as detectors and optics is greatly increased, which also reduces the manufacturing and servicing costs.

When said liquid is substantially opaque, an advantageous embodiment of the present invention has been obtained.

According to a preferred embodiment, the present invention is especially advantageous when inspecting opaque or semi-opaque liquids, as such liquids are difficult to inspect successfully with known systems. Thereby the present invention improves the detection rate and false rejection rate related to inspection of such liquids.

When said liquid comprises a suspension, an advantageous embodiment of the present invention has been obtained.

According to a preferred embodiment, the present invention is especially advantageous when inspecting suspensions, as such comprise microscopic particles that act together as an almost ideal diffuser to light, and are thus difficult to inspect successfully with known systems. Thereby the present invention improves the detection rate and false rejection rate related to inspection of suspensions or other similar substances.

When said rotation is adapted to cause any of said content, e.g. a foreign body, which has a density higher than the density of the main content, e.g. a suspension, to be pushed outwards against the container wall, an advantageous embodiment of the present invention has been obtained.

When the liquid is opaque, any foreign bodies may hide in the undetectable depths of the liquid. By spinning the container fast around the rotation axis, any objects with densities higher than the liquid, suspension, etc., is pushed outwards, against the transparent or semi-transparent container surface, where they may be detected by, e.g., a capturing device.

When said liquid comprises an insulin micro-suspension, an advantageous embodiment of the present invention has been obtained.

When said liquid is substantially transparent, an advantageous embodiment of the present invention has been obtained.

According to a preferred embodiment, the present invention is especially advantageous when inspecting transparent or semi-transparent liquids comprising low-density objects such as air bubbles. Such liquids are difficult to inspect successfully with known systems. Thereby the present invention improves the detection rate and false rejection rate related to inspection of such liquids.

When said liquid comprises a solution, an advantageous embodiment of the present invention has been obtained.

When said rotation is adapted to cause any of said content, e.g. air bubbles, which has a density lower than the density of the main content, e.g. a solution, to be pulled inwards and assemble along said rotation axis 29, an advantageous embodiment of the present invention has been obtained.

When the liquid is transparent and comprises air bubbles or other low-density content, such content is pulled inwards and assemble at the rotation axis when the container is rotated fast. Thereby the most outwards part of the liquid becomes clearer and transmits illumination more predictable, and facilitates a better detection of foreign bodies pushed outwards. Furthermore the irradiation method of the present invention provides an advantageous method of avoiding the air bubble column in the centre of the container to ruin the precise irradiation.

When said method further comprises capturing a representation of a section 48 of said container 10, an advantageous embodiment of the present invention has been obtained.

According to the present invention, capturing a representation of a section may comprise any method of establishing a signal, bitmap, analog signal, timing signal, etc., that represents one or more properties of the section, e.g. the intensity and/or color of each pixel or area, etc. A preferred method involves line scanning the surface of the container by means of a linear CCD- or CMOS-array.

When said section 48 that is captured is within said electromagnetic radiation beam 46 or its prolongation, an advantageous embodiment of the present invention has been obtained.

According to a preferred embodiment of the present invention, the detected section should be within the irradiation beam in order to ensure a proper illumination of it and any adjacent foreign bodies.

When the width of said illuminated cross-section ICS corresponds approximately to the cross-section of said section 48 as seen from the direction of said irradiation, an advantageous embodiment of the present invention has been obtained.

According to a preferred embodiment of the present invention, the electromagnetic radiation beam should be as narrow as to approximately only cover the section that is detected, and nothing more. Thereby the narrowest possible beam is determined.

The present invention further relates to an irradiation system comprising rotation means for rotating a liquid-carrying container 10, its contents 12, 13, 16, 17 or both around a rotation axis 29 and an illumination device 20 for irradiating said container 10 with an electromagnetic radiation beam 46, wherein the irradiated cross-section ICS of said container 10, irradiated by said electromagnetic radiation beam 46, is less than the cross-section CS of said container 10.

According to the present invention an advantageous irradiation system for use in container inspection systems is provided.

When said system further comprises a capturing device 23 for capturing a representation of a section 48 of said container 10, an advantageous embodiment of the present invention has been obtained.

When said system comprises means for carrying out an irradiation method, an advantageous embodiment of the present invention has been obtained.

The present invention further relates to a method for inspecting a liquid-carrying container 10 for one or more test parameters of said container 10, the contents of said container 12, 13, 16, 17, or both, comprising the steps of rotating said container 10, said contents 12, 13, 16, 17 or both around a rotation axis 29, irradiating said container with an electromagnetic radiation beam 46 from a first direction along an irradiation centre plane 31 substantially parallel to said rotation axis 29, capturing a representation of a section 48 of said container 10 from a second direction along a detection centre plane 32 substantially parallel to said rotation axis 29, and processing said representation, characterized in that the irradiated cross-section ICS of said container 10, irradiated by said electromagnetic radiation beam 46, is less than the cross-section CS of said container 10.

When the width of said irradiated cross-section ICS is less than the width of said cross-section CS of said container 10, an advantageous embodiment of the present invention has been obtained.

When the width of said electromagnetic radiation beam 46 at the position where it enters said container 10 is less than the width of said container 10 as seen from said first direction, an advantageous embodiment of the present invention has been obtained.

When said section 48 is within said electromagnetic radiation beam 46 or its prolongation, an advantageous embodiment of the present invention has been obtained.

When said irradiation centre plane 31 or its prolongation intersects said detection centre plane 32 or its prolongation in a line substantially parallel to and different from said rotation axis 29, an advantageous embodiment of the present invention has been obtained.

When the width of said electromagnetic radiation beam 46 at the position where it enters said container 10 is less than half the width, preferably less than a quarter of the width and even more preferably less than an eighth of the width of said container 10 as seen from said first direction, an advantageous embodiment of the present invention has been obtained.

When the width of said electromagnetic radiation beam 46 at the position where it enters said container 10 is less than 10 mm, preferably less than 6 mm and even more preferably less than 1 mm, an advantageous embodiment of the present invention has been obtained.

When the angle 40, 50, 60 between said irradiation centre plane 31 and said detection centre plane 32 is between 40 degrees and 140 degrees, preferably between 60 degrees and 120 degrees, and even more preferably substantially 90 degrees, an advantageous embodiment of the present invention has been obtained.

When said electromagnetic radiation beam 46 comprises visible light, an advantageous embodiment of the present invention has been obtained.

When said step of capturing a representation of a section 48 of said container 10 comprises performing a line scan parallel to said rotation axis 29, an advantageous embodiment of the present invention has been obtained.

When said step of capturing a representation of a section 48 of said container 10 comprises taking a picture with a matrix camera, an advantageous embodiment of the present invention has been obtained.

When said liquid 13 is substantially opaque, an advantageous embodiment of the present invention has been obtained.

When said liquid 13 comprises a suspension, an advantageous embodiment of the present invention has been obtained.

When said liquid 13 comprises an insulin micro-suspension, an advantageous embodiment of the present invention has been obtained.

When said liquid 13 is substantially transparent, an advantageous embodiment of the present invention has been obtained.

When said liquid 13 comprises a solution, an advantageous embodiment of the present invention has been obtained.

When said test parameters comprise existence of foreign bodies 16, 17, an advantageous embodiment of the present invention has been obtained.

When said processing comprises digital image processing, an advantageous embodiment of the present invention has been obtained.

According to a preferred embodiment of the present invention, the processing comprises digitally comparing one line-scanned line of pixels with one or more previously scanned lines in order to recognise any changes sufficiently significant to be indicative of foreign bodies, or deliberately included objects such as a mixing ball.

When said processing comprises analog signal processing, an advantageous embodiment of the present invention has been obtained.

According to an embodiment of the invention, an analog linear photo detector array may be used as capturing device and the output thereof may be processed by analog means such as, e.g., operation amplifiers arranged as comparators, or any other suitable analog means etc. It is noted that also analog/digital hybrid processing means are within the scope of the present invention, e.g. digitally processing the output of the mentioned analog photo detector array.

When said step of capturing a representation is repeated several times, and said step of processing said representation comprises comparing said representation with at least a part of at least one further representation of a section 48 of said container 10, an advantageous embodiment of the present invention has been obtained.

According to a preferred embodiment of the invention, the capturing device is continuously capturing representations which are processed simultaneously, maybe with a little delay for preparing the processing. In an alternative embodiment the capturing device is synchronized with the rotation rate of the container or its content, and captures images according thereto in order to ensure that images from all sides of the container or content has been captured.

The present invention further relates to a method for inspecting a liquid-carrying container 10 for one or more test parameters of said container 10, the contents of said container 12, 13, 16, 17, or both, comprising the steps of rotating said container 10, said contents 12, 13, 16, 17 or both around a rotation axis 29, irradiating said container with an electromagnetic radiation beam 46 from a first direction along an irradiation centre plane 31 substantially parallel to said rotation axis 29, capturing a representation of a section 48 of said container 10 from a second direction along a detection centre plane 32 substantially parallel to said rotation axis 29, and processing said representation, characterized in that the width of said electromagnetic radiation beam 46 at the position where it enters said container 10 is less than the width of said container 10 as seen from said first direction.

The present invention further relates to an inspection system for liquid-carrying containers 10 comprising
  rotation means for rotating said container 10, its contents 12, 13, 16, 17 or both around a rotation axis 29,
  an illumination device 20 for establishing an electromagnetic radiation beam 46 for irradiating said container from a first direction along an irradiation centre plane 31 substantially parallel to said rotation axis 29,
  a capturing device 23 for capturing a representation of a section 48 of said container 10 from a second direction along a detection centre plane 32 substantially parallel to said rotation axis 29, and
  processing means for processing said representation,
characterized in that
  the irradiated cross-section ICS of said container 10, irradiated by said electromagnetic radiation beam 46, is less than the cross-section CS of said container 10.

According to the present invention an advantageous inspection system for liquid-carrying containers is provided.

When said system comprises an irradiation system, an advantageous embodiment of the present invention has been obtained.

When said system comprises means for carrying out a method of irradiating a liquid-carrying container, an advantageous embodiment of the present invention has been obtained.

When said system comprises means for carrying out a method for inspecting a liquid-carrying container, an advantageous embodiment of the present invention has been obtained.

BRIEF DESCRIPTION OF THE DRAWINGS

The invention will in the following be described with reference to the drawings where
FIG. 1 illustrates an embodiment of a container for use with the present invention,
FIG. 2 illustrates a typical inspection system setup,
FIG. 3A-3C illustrate embodiments of conventional inspection systems.

DETAILED DESCRIPTION

Figure 4:
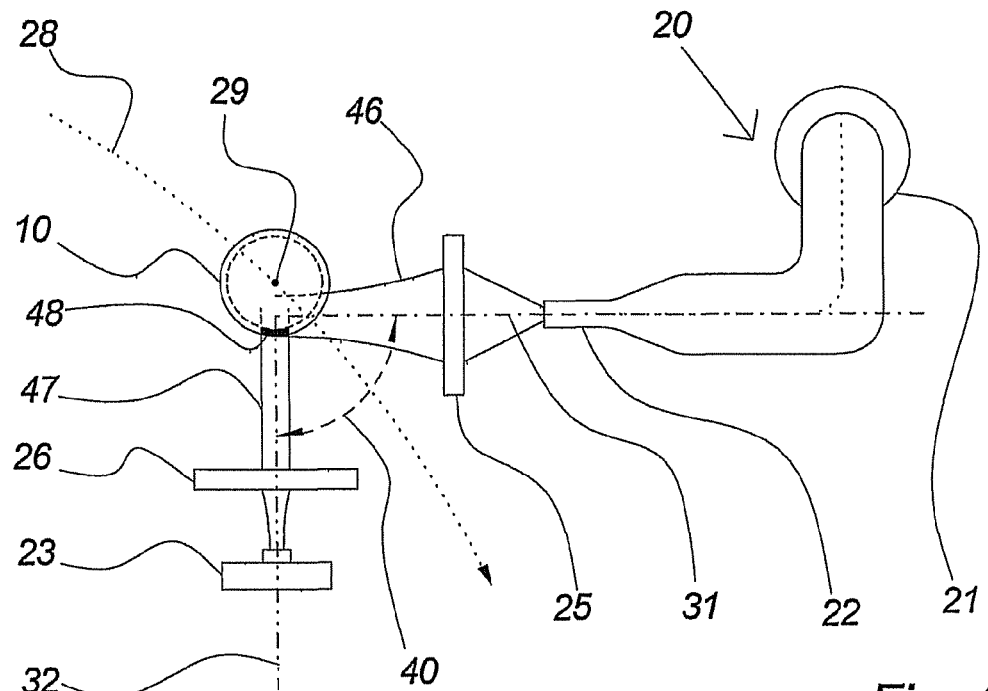
FIG. 4-6 illustrate different embodiments of the present invention.

According to the present invention, several types of containers may be inspected by means of an embodiment of the invention. The containers are preferably containers for medication or other pharmaceutical product, such as, e.g., ampoules, vials, cartridges, syringes, etc., but may be of any container type suitable for inspection by electromagnetic radiation and detection.

Further, according to the present invention, the reference to a liquid-carrying container should be understood in a broad sense, i.e. a container at least carrying a liquid or a substance which, as a whole, substantially acts as a liquid under certain conditions, e.g. liquids, suspensions, solutions, emulsions, dispersions, etc. Further, it follows from the nature of the invention that at least some containers may additionally carry items not to be regarded part of the "liquid", e.g. foreign bodies, e.g. glass fragments, and/or required items, e.g. a mixing ball.

FIG. 1 illustrates one of several possible types of containers according to the present invention. The container 10 comprises an outer cylindrical surface 14 indicated by a solid line and an inner cylindrical surface 15 indicated by a dashed line. In the bottom, a plunger 18 seals the container, and in the top it is sealed with a cap 11, possibly comprising a rubber membrane. A substance 13 fills most of the space 12 inside the container 10. The particular container of FIG. 1 further comprises a mixer ball 17 and a foreign particle 16, e.g. a piece of hair. It is emphasized that the container shown in FIG. 1 is just an example of a container to by inspected by an apparatus according to the present invention, and any suitable container and/or content is within the scope of the present invention.

The cylindrical body of the container 10 should be transparent, translucent, or at least penetrable by electromagnetic radiation, preferably light. It is preferably clear, smooth and even, but may alternatively be coloured, and/or comprise vertical or horizontal indications, markings, grooves, etc. It is preferably made of glass, but may alternatively be made of a synthetic material such as plastic, etc. Instead of being open in the bottom to allow the plunger 18 to be inserted and operated, it may for other purposes as well be closed. In FIG. 1 the container 10 is shown having a neck in the top end, to facilitate a cap. In alternative embodiments the neck may be designed in any suitable form, or be omitted, hence causing the body of the container to simply resemble a pipe of glass.

The cap 11 may be any suitable type of container top closure, and may typically comprise a rubber membrane suitable for penetration by a syringe needle. The plunger 18 is preferably a rubber plunger, but may be of any suitable material and form. For containers only operated through the top opening, the plunger may be omitted, and the container provided with a suitable bottom.

The mixer ball 17 is preferably made of glass, but may be of any suitable material, or omitted at all. It is typically provided in suspensions or substances 13 that tend to curdle or settle over time. By sufficiently spinning, shaking or vibrating the container, the mixer ball will cause the substance to homogenize.

The container 10 may comprise any kind of substance 13, typically a pharmaceutical mixture, e.g. an insulin microsuspension. According to the present invention, the inspection apparatus may detect foreign particles or other defects within any kind of substance, e.g. liquids, suspensions, solutions, emulsions, dispersions, etc. The empty space 12 inside the container 10 may comprise air, vacuum, a particular gas or mixture of gasses, etc.

The foreign particle 16 indicates an undesired object comprised by the substance 13. The purpose of the present invention is to detect such undesired objects, and cause the container in question to be rejected or at least handled in a particular way.

FIG. 2 illustrates in principle a common illumination and detection part of container inspection systems. It comprises an illumination device 20, comprising a light source 21 and an optical light guide array 22 adapting the light beam into having a rectangular cross-section with a height at least corresponding to the container height. The optical light guide array may thus be said to stretch an irradiation centre plane from the vertical centre of the optical light guide array 22 to the vertical centre of the container 10. The light source 21 may, e.g. comprise a lamp, LED, etc., and possibly light adapting means such as reflectors, filters, lenses, diffusers, etc. The illumination device illuminates the container 10, possibly through a light adapting means 25, e.g. a filter, a diffuser, a lens, etc. FIG. 2 further comprises a capturing device 23, comprising a detection array 24, e.g. a linear CCD array comprising 1024 pixels arranged in a vertical line, or any other camera or detection device. The capturing device is coupled to processing means, which are not shown. The detection array 24 detects light transmitted through or reflected or scattered from the container 10 and/or its content, and a detection centre plane may thus be said to exist between the vertical centre line of the container 10 to the detection array 24. A light adapting means 26, e.g. a filter, a diffuser, a lens, etc., may possibly be provided between the container 10 and the capturing device 23.

The container 10 may possibly be rotating around a rotation axis 29, e.g. its vertical axis, as indicated by arrow 27, or it may have been rotated at a high rate, e.g. 6000 rpm, and then stopped, causing the contents, if sufficiently fluid, to remain circulating around the rotation axis 29 inside the container, thereby causing any particles or objects with densities higher than the liquid to be pulled outwards, i.e. towards the cylindrical surface of the container.

The container 10 may further possibly be travelling through the detection area along a, typically, horizontal line of motion, as indicated by the arrow 28. Several containers may, e.g., be placed in a carousel, and thus rotated through the detection area. In such a system, instead of pausing the carousel for each container's inspection, the illumination device 20 and/or the capturing device 23 may be adapted to track the moving container 10, e.g. by travelling along routes parallel to the container's route. When a container has been inspected, the illumination and/or capturing devices may be relocated to their original position, ready to inspect the next container. Instead of moving the illumination and/or detection devices, it is possible to provide a system of mirrors, lenses, prisms or solid state devices that rotate or moves in order to track the container.

FIGS. 3A to 3C illustrates different illumination methods known from prior art, and correspond generally to embodiments as the one shown in FIG. 2, but seen from above. They comprise an illumination device 20 comprising a light source 21 and an optical light guide array 22, a container 10 for inspection, a capturing device 23 and possibly one or more light adapting means 25 and 26. In the figures are further indicated the rotation axis 29 and the irradiation centre plane 31 stretching between the vertical centre line of the optical light guide array 22 and the vertical centre line of the container 10, and the detection centre plane 32 stretching between the vertical centre line of the container 10 and the vertical centre line of the capturing device 23, both centre planes resembling lines when seen from above, illustrating the direction from which the container 10 is illuminated, and the direction from which the detection is performed. Also probable light beam 36 and detection field of view 37 are indicated.

In FIG. 3A the illumination is directed towards the centre of the container 10, i.e. the rotation axis 29, and the capturing device 23 is placed in the opposite direction, causing the angle 33 between the irradiation centre plane 31 and the detection centre plane 32 to be 180 degrees. In such an embodiment, the illumination is pointed directly towards the capturing device, possibly causing saturation or even blooming when inspecting transparent container contents or containers with, e.g., an amount of air above the content surface. When the container content is, e.g., a suspension, it acts as an almost ideal diffuser to the illumination, thereby causing any particle to be very uniformly illuminated and thereby avoids shadows. Objects or particles in the container contents from the capturing device's point of view may appear darker or lighter than the background, i.e. the main contents, e.g. a suspension, depending on the refractive and translucence properties of their surface and composition. Hence, a transparent object, e.g. a glass mixing ball, may appear lighter than the background as it transmits more light than the suspension it replaces, whereas an opaque object may appear darker than the background because it blocks the light. A particle is thus only detectable if the difference between its apparent colour, e.g. light grey for glass particles and dark grey for opaque particles, and the colour of the diffuse, medium grey background is sufficiently significant.

In FIG. 3B the illumination is directed towards the centre of the container 10, i.e. the rotation axis 29. The capturing device is placed such that the angle 34 between the irradiation centre plane 31 and the detection centre plane 32 is between 90 and 180 degrees, e.g. 120 degrees. Compared to the embodiment of FIG. 3A, this embodiment, thus, causes the container and particles to be illuminated obliquely from behind, as seen from the detection device. Such an embodiment is less liable to cause saturation or blooming when inspecting transparent container contents or containers with, e.g., an amount of air above the content surface. Objects or particles in the container contents from the capturing device's point of view typically appear as in the embodiment of FIG. 3A. For the size of angle 34 is typically selected the angle where the detection device 23 measures the highest average intensity, i.e. the angle where the container and content, as seen from the capturing device, seems as bright as possible, and/or the angle where the background, i.e. the main contents, e.g. a suspension, appear as homogeneous as possible. This angle may, e.g., be determined from experience or by experiments. By applying that criterion to the angle, it is sought to establish the highest possible contrast between the container content and a possible foreign particle blocking or transferring the light, and/or causing the background to provide the lowest possible contrasts, i.e. optical dynamic range, itself, and thereby establish the best conditions possible for detecting such particle.

In FIG. 3C the irradiation and detection centre planes and the angle there between are as in FIG. 3B, but the illumination device 20 has been moved farther away, and the light beam 36 controlled by a mirror 35, or other suitable light direction means. Thereby a higher degree of freedom has been obtained, regarding the physical positioning of the illumination device 20. Moreover the irradiation centre plane 31 may be caused to track a possibly moving container by means of rotating the mirror 35. A corresponding mirror-provided setup may in a further embodiment be provided for the capturing device 23, and the detection centre plane 32.

FIG. 4 illustrates an embodiment of the present invention. In general it comprises the same elements as described above regarding FIGS. 1, 2 and 3A to 3C. They are, however, arranged in a different way in order to obtain a surprising and advantageous effect. FIG. 4 comprises a container 10 to be inspected, preferably corresponding to the description above regarding FIG. 1. It further comprises an irradiation device 20 comprising an electromagnetic wave source 21, e.g. a light source, and an electromagnetic wave guide array 22, e.g. an optical light guide, establishing an electromagnetic radiation beam 46 with a preferably rectangular cross-section having a height preferably corresponding to at least the container height. The electromagnetic wave source 21 emits an electromagnetic radiation with a suitable wavelength that does not alter the container or its contents undesirable, and for which a suitable detector exists. The electromagnetic radiation is preferably visible, "white" light, i.e. comprising light of several different wavelengths, but may alternatively be coloured light, infrared light, ultraviolet light, x-rays, microwaves, radio-waves, etc. The electromagnetic wave source 21 may, e.g. comprise a lamp, one or more LEDs, a conventional light bulb, a short arc lamp, a fluorescent tube, a laser beam generator, etc., preferably a tungsten halogen lamp, and possibly light adapting means such as reflectors, filters, lenses, diffusers, etc. The irradiation device illuminates the container 10, preferably through a beam adapting means 25 suitable for the kind of electromagnetic radiation utilized, e.g. a filter, a diffuser, a lens, etc., preferably comprising a collimating lens and focusing means. A suitable beam adapting means 25 may even facilitate the, e.g., optical light guide array 22 to have a height less than the container, if properly diverging the light. According to a preferred embodiment of the invention, the electromagnetic radiation beam 46 is, when it reaches the container surface, preferably a narrow, collimated beam, i.e. of substantially parallel light rays, and the width of the beam is less than the container's width as seen from the direction of illumination, e.g. less than the container's diameter, preferably less than the half of the container's width, and most preferably as narrow as possible. In applications where any foreign bodies may be expected to comprises a significant width, the electromagnetic radiation beam should be sufficiently wide to illuminate such bodies. FIG. 4 further comprises a capturing device 23, preferably comprising a detection array, e.g. a linear CCD or CMOS array comprising 1024 pixels arranged in a vertical line, but may alternatively comprise a digital camera or CCD or CMOS matrix camera, an array of photo detectors, or any other device suitable for detecting the desired kind of electromagnetic radiation. The capturing device captures a representation of a section 48 of the container. The capturing device comprises means for communicating results of the detection, e.g. sequential line scans or digital images, and is coupled to processing means, e.g. a digital signal processor, a central processing unit CPU, a microprocessor, a programmable gate array, dedicated logics, etc., which are not shown. The capturing device detects light transmitted through or reflected or scattered from the container 10 and/or its content. A beam adapting means 26, e.g. a filter, a diffuser, a lens, etc., may possibly be provided between the container 10 and the detection device 23, preferably in order to focus and adapt the image of the section 48 of the container to the size of the detection array, preferably a collecting lens, converging lens, or other focusing means. In a preferred embodiment, the beam adapting means 26 is arranged to reduce a narrow, vertical line section 48 of the container, e.g. 70 μm wide, to the detection width of the capturing device, e.g., 10 μm.

FIG. 4 further illustrates an irradiation centre plane 31 stretched between the optical light guide array 22 and the container 10, and a detection centre plane 32 stretched between the container 10 and the capturing device 23, illustrating the direction from which the container 10 is illuminated, and the direction from which the detection is performed.

In FIG. 4 the irradiation is directed towards the part of the container 10 that is captured by the capturing device. Due to the electromagnetic radiation beam 46 being narrower than the container's width, and preferably even narrower than half its width, the container is not fully illuminated. The electromagnetic radiation beam should thus be directed towards the section 48 that is being captured, in order to preferably illuminate that part of the container only. As it is the container's content, e.g. a suspension, that causes the background to appear extremely uniform and homogeneous in prior art embodiments, e.g. FIGS. 3A-3C, because the, e.g., suspension act as an almost ideal diffuser, this effect is not established to the same extent in embodiments of the present invention, e.g. FIG. 4, as only a smaller part of the, e.g., suspension is illuminated. The background in an image captured with the embodiment of FIG. 4 may thus appear a little more coarse and grainy compared to the embodiment of, e.g., FIG. 3B. The less diffusion, however, also reduces the uniformness by which any particle is illuminated in the prior art embodiments, and thus does not avoid shadows to appear in the embodiment of FIG. 4. Whereas the less homogenous background and the shadows until now have been considered problems and sought to be avoided, the present invention utilizes these effects for improving the inspection system. By illuminating the container according to the principles of the present invention, the obtainable optical dynamic range of the resulting images or representations is higher than for earlier systems. In order to be able to improve correct separation of particles from the background, it is important that the difference between the background and the particles when looking on the captured representation(s) is as high as possible. In conventional systems this is, as described, sought obtained by causing the background to be as homogenous as possible, i.e. comprising a very small optical dynamic variation. Foreign bodies, as well as desired objects, e.g. mixing balls, may appear lighter or darker than the background reference, and that difference may be sufficient to detect the particles, but still the optical dynamic range is small. With the present invention the optical dynamic variation comprised by the background itself may typically be a little larger, as the background appear a little more grainy, but on the other hand the optical dynamic range when a particle is present is increased significantly more than the increase in the background's optical dynamic variation. Thus, the absolute difference between the background reference and the representation of a foreign body is significantly increased by the present invention. This improvement is, among other things, Entering light is collimated and provides the best illumination for detection of a broad range of particle types. As entering light progresses through the distance from entry point to caused by the shadows typically established by foreign bodies when only a little part of the container is illuminated. When, e.g., a glass particle, e.g. a glass mixing ball or an undesired glass fragment, is captured, it appears according to the present invention as a light object with a dark shadow. The background reference is typically somewhere in between. The image processing means may thus, e.g., detect a light-to-dark transition, i.e. first the object's representation followed by its shadow's representation. Instead of providing an optical dynamic range ranging from the background reference to either light or dark, the present invention provides an optical dynamic range ranging from light to dark. If, for some reason, an object does not establish both a light and a dark representation, the object may of course still be detected by a system according to the present invention, as the system typically inherits the detection algorithms of conventional system. Experiments show that the detection rate for an inspection system implementing the illumination method of the present embodiment is improved and the false reject rate reduced, compared to common illumination methods illuminating the full container. The angle 40 separating the irradiation centre plane and detection centre plane should preferably be between 40 degrees and 140 degrees, more preferably between 60 degrees and 120 degrees, and even more preferably about 90 degrees. When selecting the size of angle 40, care should be taken not to select angles where the part of the illumination that is reflected directly from the outer cylindrical surface of the container is reflected directly into the capturing device, possibly causing saturation or even blooming. The angles to avoid may, e.g., be determined from experiments.

For transparent liquids, solutions, etc., a problem in prior art is that any air bubbles or other content having densities lower than the main content, i.e. the liquid, assemble in the centre of the container, along the rotation axis 29, when the liquid is rotated. When illuminating the full width of the container light is reflected, scattered and diffused uncontrollably upon entering this air bubble column, and this uncontrolled illumination may impede detection of foreign bodies. By utilizing the illumination method of the present invention, i.e. by illuminating only a part of the container cross-section, preferably less than half of the container cross-section, and avoiding illuminating this centre column, a very significant improvement is obtained. Illumination of the section 48 without illumination of any possible air bubble centre column may be provided by an illumination system according to the present invention, as only a part of the container is illuminated by a narrow light beam coming from the side, as seen from the direction of detection.

It is further noted, that an embodiment where the container is lying down, the rotation axis 29 being horizontal, or the container being placed in any direction, and the electromagnetic irradiation beam and the detection field of view being rearranged accordingly, is perfectly within the scope of the present invention, even though it is not explicitly mentioned for each embodiment described.

Figure 5:
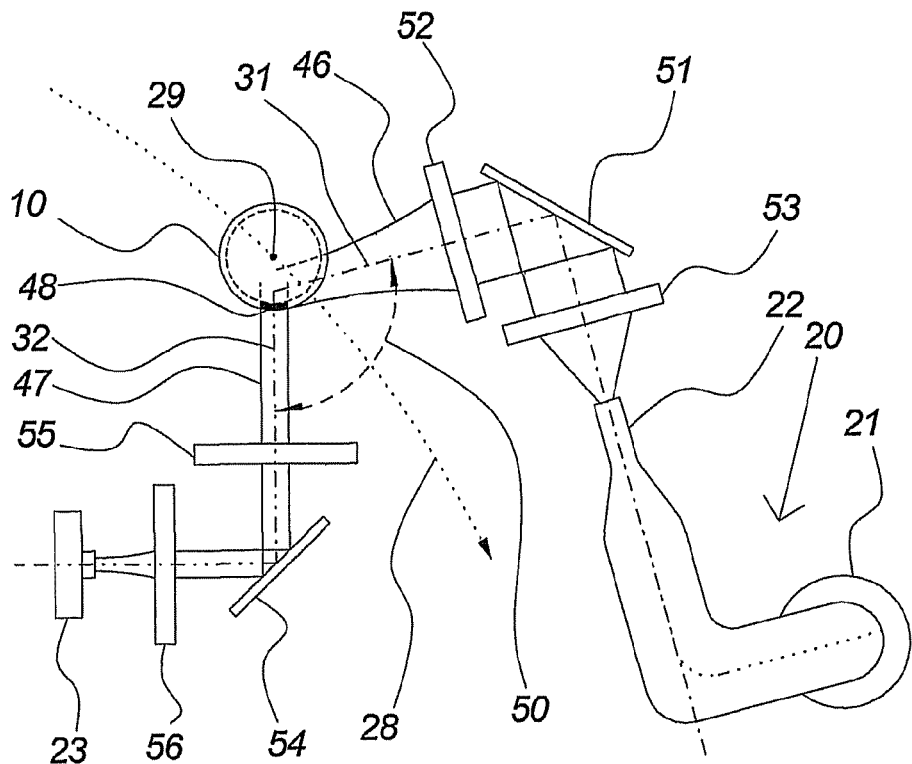

FIG. 5 illustrates and alternative embodiment of the embodiment of FIG. 4, where mirrors 51 and 54 are provided for enabling rearranging the components, and/or for adapting characteristics of the illumination. It is emphasized that the mirrors may be any means suitable for directing electromagnetic radiation in a desired direction, e.g. mirrors, reflectors, e.g. parabolic reflectors, prisms, TIR-prisms, etc. The mirror means may additionally be arranged to adapt characteristics of the electromagnetic radiation, e.g. polarization, spectral contents, focus, collimation, etc. In further alternative embodiments, several mirrors may be arranged in order to facilitate the desired positioning of the components, and/or in order to enable the desired or necessary adaptations of the electromagnetic radiation beam 46 and/or detection field of view 47. The embodiment of FIG. 5 further comprises several beam adapting means 52, 53, 55, 56, as the beams may be adapted at any suitable leg. Each beam adapting means 52, 53, 55, 56 may comprise any means suitable for the kind of electromagnetic radiation utilized, e.g. filters, diffusers, lenses, etc. The electromagnetic irradiation beam 46 is preferably adapted by means of collimating means and focusing means, and the detection field of view 47 is preferably adapted by means of focusing means.

In FIG. 5 the angle 50 separating the irradiation centre plane 31 and detection centre plane 32 is shown as being about 105 degrees. The angle 50 should preferably be between 40 degrees and 140 degrees, more preferably between 60 degrees and 120 degrees, and even more preferably about 90 degrees.

FIGS. 4 and 5 further indicates a possible line of motion 28 of the container 10, e.g. corresponding to the motion applied by a carousel holding several containers sequentially brought through the inspection area. The line of motion may in alternative embodiments resemble a substantially straight line, or any other course of motion, horizontal, vertical or both, suitable in the context in which the inspection system is implemented. In such systems where the containers are transported past the inspection system for inspection, the motion may be stopped during the inspection, the motion may be relatively slow compared to the inspection duration, or, as a preferred embodiment, the illumination device and/or detection device is adapted to be able to track the moving container until the inspection is completed, and then return to their starting point, ready for the subsequent container. As described above, enabling the illumination and/or detection devices to track the container may be established by enabling the illumination and/or detection devices to rotate or reciprocate, or, with the embodiment of FIG. 5, enabling the mirror 51 and/or the mirror 54 to rotate or reciprocate. Alternatively lenses, prisms, solid state devices, etc., may be provided to enable tracking the container.

Figure 6:
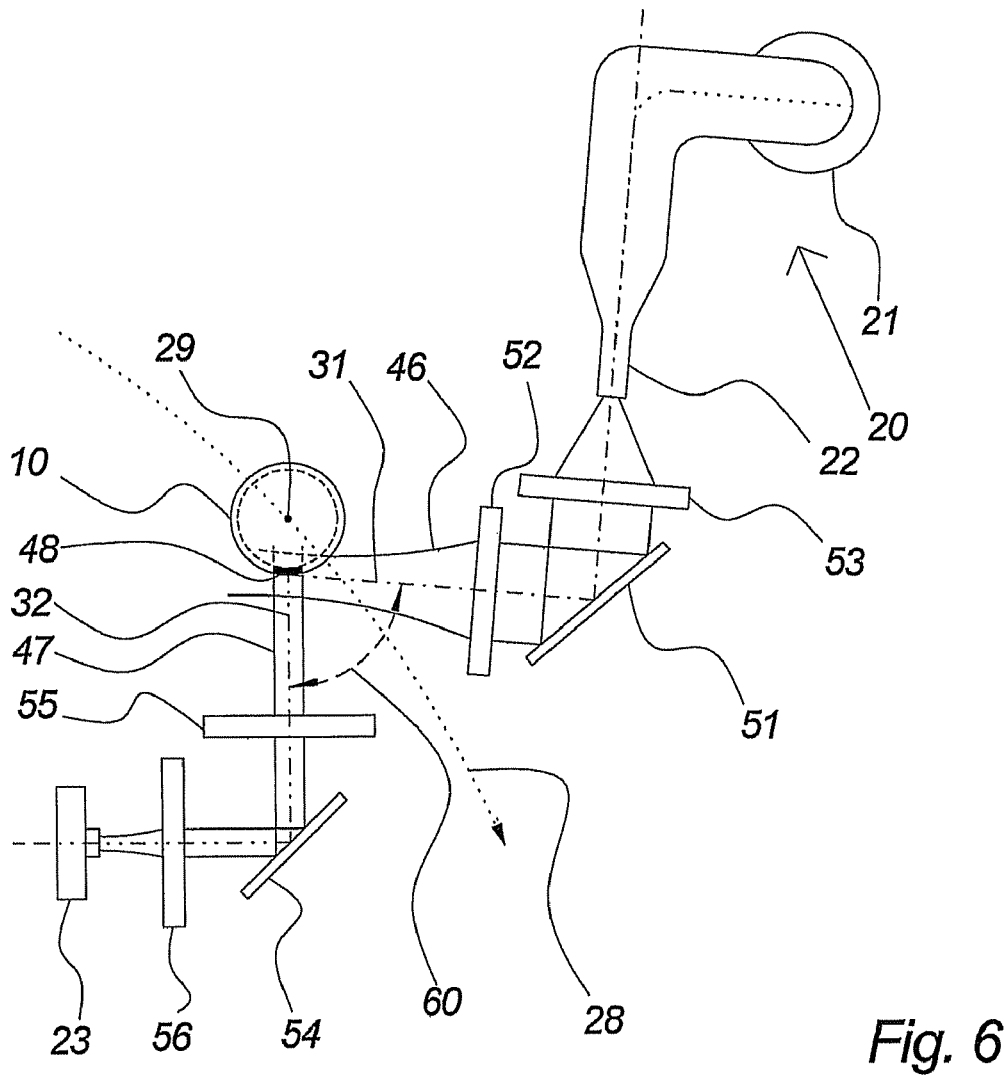

FIG. 6 illustrates a further alternative embodiment of the present invention. It comprises components arranged similar to FIG. 5. In FIG. 6 the angle 60 is illustrated as being about 85 degrees, and should preferably be between 40 degrees and 140 degrees, more preferably between 60 degrees and 120 degrees, and even more preferably about 90 degrees. In FIG. 6 the electromagnetic radiation beam 46 is, as in the embodiments of FIGS. 4 and 5, directed towards the section 48 that is being captured, but in FIG. 6 the irradiation centre plane 31 is displaced so that part of the beam goes past the container without hitting it. Thereby the container is only exposed to an effective irradiation being less than the full width of the beam. The embodiment of FIG. 6 where the irradiation is displaced in order to only hit the container by part of the beam may be advantageous when it is not possible to establish a suitably narrow electromagnetic radiation beam 46. By properly changing the displacement, the width of the effective beam may range from extremely small, when only the side of the beam slices the container, to as wide as the full beam.

Figures 7A, 7B, 7C, 7D:
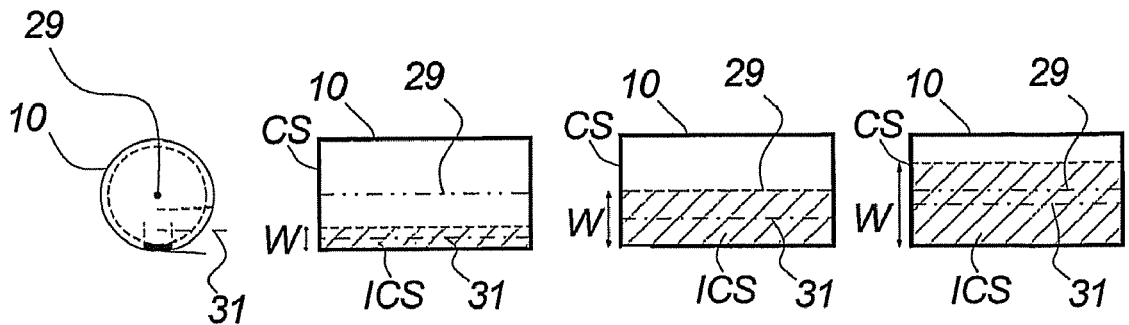
FIG. 7A-7D illustrate a detail of the concept of the present invention.

FIGS. 7A to 7D illustrate an aspect of an embodiment of the present invention in more detail. FIG. 7A illustrates a container 10 seen from above, corresponding to FIGS. 4-6. One possible embodiment of the electromagnetic radiation plane 31 is shown, as well as the rotation axis 29.

FIGS. 7B-7D illustrate a cross-section of the container as seen from the side from the direction from which it is illuminated, i.e. along the electromagnetic radiation plane 31. This plane is in FIGS. 7B, 7C and 7D shown from the end instead of from above, as the container is seen from the side. The cross-section CS of the container comprises the full width of the container as seen from the side, and corresponds for cylindrical containers to the diameter of the container. In FIGS. 7B-7D is also shown an irradiated cross-section ICS, which is the part of the container's cross-section CS that is irradiated by the electromagnetic radiation beam 46. The width W of the irradiated cross-section ICS may, e.g., be expressed as relative to the width of the container's cross-section CS, and the width W should according to a preferred embodiment of the present invention, be less than the width of the cross-section CS. Also the rotation axis 29 is shown in FIG. 7B-7D.

FIG. 7B thus illustrates a cross-section CS of the illustrated container 10 when seen from the direction of the electromagnetic radiation beam 46. Only a part of the cross-section is irradiated by the irradiation source and according to a preferred embodiment of the invention, the irradiated cross-section ICS of this and the following embodiments should be less than the cross-section CS of the container.

Preferably, the irradiated cross-section ICS should be sufficiently large to cover the section, e.g. the section 48 of FIG. 4, 5 or 6, which is captured by the capturing device 23 also of FIG. 4, 5 or 6.

The illustrated embodiment is preferred due to the fact that the width W of the irradiated cross-section ICS is less that half the width of the complete cross-section CS.

FIG. 7C illustrates a further embodiment within the scope of the invention. In this embodiment the irradiation arrangement of FIG. 4, 5 or 6 has been rearranged and adjusted to irradiate a somewhat larger cross-section ICS than illustrated with respect to FIG. 7B, namely now with a width W of the irradiated cross-section ICS which is approximately half the width of the cross-section of the container.

FIG. 7D illustrates a further embodiment within the scope of the invention. In this embodiment the irradiation arrangement of FIG. 4, 5 or 6 has been rearranged and adjusted to irradiate an even larger cross-section ICS than illustrated with respect to FIGS. 7B and 7C, namely now with a width W of the irradiated cross-section ICS which is larger than half the width of the cross-section CS of the container 10.

Figure 8:
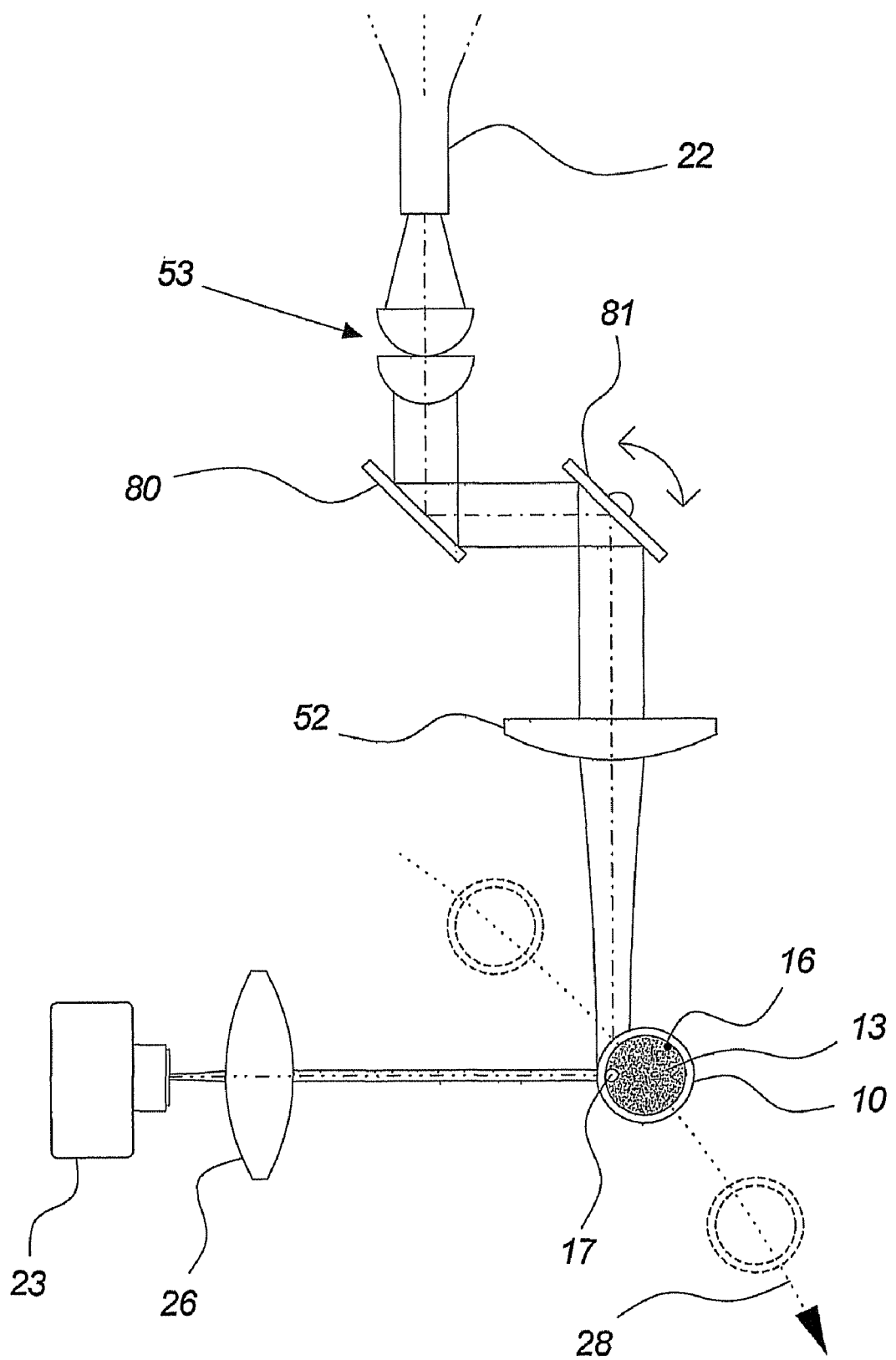
FIG. 8 illustrates a preferred realization of the present invention, and
  FIG. 9A-9B comprise experiment results.

FIG. 8 illustrates a practical example of an optical system according to one of the embodiments described above regarding FIGS. 4-6. FIG. 8 comprises an optical light guide array 22 emitting an approximately rectangular cross-section light beam having a height approximately corresponding to at least the height of the illuminated container, and a width as small as practically possible, e.g. about 1 mm. The light beam is adapted by a light adapting means 53, preferably a cylindrical collimating lens, and is then turned 90 degrees by a turning mirror 80, thereby directing the collimated light beam towards a pivoting mirror 81 facilitating tracking a moving container. The light beam is focused by a cylindrical projection lens 52, which focuses the light beam at the container 10, as well as, in combination with the pivoting mirror, causes the light beam to be displaced in a direction perpendicularly to the light beam's direction. The light beam that leaves the cylindrical projection lens 52 is directed towards the desired section of the container 10, and correspond to the electromagnetic radiation beam 46 referred to in the previous figures. The width W of the electromagnetic radiation beam's cross section ICS, e.g., 5 mm.

FIG. 8 further comprises a container 10, e.g. having a width of 11 mm. It may, e.g., comprise an insulin micro-suspension 13 and a glass mixing ball 17 for facilitating homogenisation of the suspension by shaking, vibration, spinning, etc. It may further, e.g., comprise a foreign body 16. By the mentioned widths is ensured that less than the container's cross-section, and even less than half its cross-section, is illuminated by the light beam.

FIG. 8 further comprises a camera sensor chip 23 located inside a conventional camera suitable for the inspection method utilized, e.g. suitable for line scanning and fast read out from its image registers. The camera may have a detection field of view at the sensor chip with a width of, e.g., 10 μm. An objective lens 26 is placed in the detection field of view 47 in order to establish a detection field of view at the container surface of, e.g., 70 μm wide.

FIG. 8 further comprises a line 28 indicating the movement of the container 10, and indications of previously and subsequently inspected containers, shown in dashed lines.

FIGS. 9A and 9B show the results of an experiment. FIG. 9A is a line scanned image of a container established by an embodiment corresponding to the embodiment of FIG. 3A, i.e. where the container is illuminated from behind, and in its full width. In the image may be recognised the cap 11, an air-filled gap 12 at the container's neck, a insulin micro-suspension 13 and a rubber plunger 18. It is also possible to recognise a glass mixing ball 17, as it appear lighter than the suspension background 13, as it transmits light better than the suspension.

FIG. 9B is a line scanned image of a container established by an embodiment of the present invention corresponding largely to the embodiments shown in FIGS. 4 and 8. From this image the same objects as in FIG. 9A may be recognised, even though they appear differently. The light-filled gap 11 does not cause blooming because of direct, unfiltered illumination of the detection array, but appear instead relatively dark, as the air does not scatter and diffuse the light nearly as well as the suspension 13. The suspension in FIG. 9B looks a little less homogenous or grainy as in FIG. 9A, as it does not comprise light from as big a volume as in FIG. 9A because of the illumination coming from an angle of about 90 degrees. The glass mixing ball 17, which in FIG. 9A appear only as a light, blooming spot, appear in FIG. 9B as a light mark adjacent to a dark mark, i.e. with intensities at both sides of the background's average intensity. In preferred embodiments of the present invention, the inspection method, except for the illumination of the container, may be one of the methods described in PCT-application WO 92/14142, hereby incorporated by reference, or any other suitable method. A preferred embodiment comprises inspecting entities comprising liquid-carrying containers for one or more test parameters of the liquid, the container, or both, by irradiating, rotating, and axially line scanning the entities along a line parallel with the axis of rotation by detecting radiation transmitted, reflected, diffracted, or scattered from this entity, comprising:

rotating the entity according to a predetermined rate profile having one or more periods of constant angular velocities, line scanning the container axially during the periods of constant angular velocities, and comparing pixel values of said line scans with set references; and/or rotating the entity according to a predetermined rate profile comprising rates of rotation causing the liquid to circulate and foreign bodies having densities higher than the liquid to accumulate at the container wall, bringing the container to a standstill with the liquid rotating, line scanning the entity axially before the rotation of the liquid is substantially reduced, digitally filtering the pixel values of said line scans, and comparing the filtered values with predetermined references.

Thus, in a preferred container inspection embodiment the analysis of scanned data comprises image analysis of the unfolded image consisting of scans of the desired part of the surface of the container, and in foreign body inspection, according to the invention, where the analysis of scanned data comprises analysis of successive scans of the contents of the container.

The expression "unfolding" is intended to mean the construction of a two-dimensional representation of one-dimensional line scans of the container. Thus, an unfolded image of stationary parameters may comprise an electronic representation of pixel values obtained from individual line scans during one or more 360 degrees revolutions of the rotating container, i.e. one dimension of the image being the height and the other the perimeter of the container; and an unfolded image of dynamic parameters may comprise an electronic representation of pixel values obtained at different times, i.e. the one dimension of the image being the height of the container and the other the time at which the same individual section 48 of the container was scanned.

In order to provide an unfolded image of the required resolution and quality for the test parameter to be inspected according to the invention, an unfolded image of the container may be provided by rotating the container either stepwise or continuously according to a predetermined rate profile which optionally has one or more periods of constant angular velocities during the inspection, and scanning the rotating container at a suitable scanning rate.

In a preferred embodiment, the rotation is chosen to be stepwise such that each individual section 48 of the container can be scanned for a sufficiently long time to provide the required resolution of the unfolded image. Thus, for a given rate of stepwise rotation and an appropriate scanning rate of the detection apparatus, a whole line of sections parallel to the axis of rotation may be scanned within an incremental step of the angular rotation. In another embodiment, non-parallel e.g. helix type scanning may be applied to unfold a container image at relatively higher rates of rotation provided each individual scanned section of the container can be unambiguously retrieved.

For stationary images, or container inspection, rates of angular rotation and scanning rates of the detection apparatus are chosen such that line scans are provided at relatively low rates and such that each individual section of the container may be scanned once or several times through successive revolutions to provide several unfolded images. In a preferred embodiment optional periods of constant angular velocity generally occur at rotation rates below 2000 rpm, particularly below 1500 rpm, preferably about 1200 rpm.

For dynamic images, i.e. foreign body detection, rates of angular rotation and scanning rates of the detection apparatus are chosen such that line scans may be provided at relatively high rates of rotation of the entity to be inspected. During these high rates of rotation line scans are provided differentially such that individual sections are scanned successively at given heights during one or more revolutions.

The rate profile comprises rates of rotation that causes the liquid to circulate and bodies having densities larger than that of the liquid to accumulate at the container wall. Thus, even for nontransparent suspensions and emulsions, foreign bodies at the container wall can be detected. In a preferred embodiment detection of foreign bodies in the liquid having densities larger than that of the liquid is performed while the liquid is rotating at a rate from about 10000 rpm to about 2000 rpm, preferably from about 6000. Further, in another embodiment the total inspection time, including the scanning, is less than 1000 ms, preferably less than 500 ms, most preferred about 250 ms. Within the present context, the expression "differentially" is intended to designate differentially in time or differentially in distance. Thus, for a circulating liquid contained in a container at rest, line scans may be provided "differentially in time" for given sections of the container by successive measurements of the same container sections but different sections of the rotating liquid. Also, for a rotating container, line scans may be provided "differentially in distance" for different sections of the perimeter by successive measurements of different container sections at different times.

In a preferred embodiment the entity is irradiated with electromagnetic radiation and the transmitted, reflected, diffracted or scattered radiation is detected by a linear array of radiation detectors and stored digitally, preferably in a frame store memory and a matrix filter. Analysis of recorded data comprises electronic comparison of actual pixel values or manipulated pixel values, e.g. values of individual pixels or values of groups of pixels that may be transformed by multiplication, addition, subtraction, or other transformations such as logarithms, means and standard deviations. Thus depending on the test parameter to be inspected, individual pixels, i.e. pixel addresses, are chosen and their values applied for the comparison. Thus, in preferred embodiments individual pixels and groups of pixels are selected to analyze recorded data of one or more test parameters of the liquid and the container, respectively.

In a preferred embodiment one or more test parameters of the liquid is selected from the group consisting of:
  type of liquid, including clear solution, emulsion, and suspension;
  liquid specification, including amount and intended content, concentration of components, color, transmittance, and mixer ball; and
  foreign matter, including foreign liquids and bodies, suspended particles, impurities and undesired flocculation, growth of crystals and biological organisms.

Further, in a preferred embodiment one or more test parameters of the container are selected from the groups consisting of:
  container specification, including shape, bottom, cap, labels, bar code, plunger, fill level, color and transmittance;
  container defects, including flaws, cracks, air bubbles and particles entrapped in the container wall, and weakenings; and
  container contamination, including dirt and dust, material entrapped between the plunger and container wall.

In a preferred embodiment, an inspected entity exhibiting one or more unacceptable test parameters of the liquid, the container, or both is identified and separated from containers having acceptable test parameters.

A preferred embodiment of an inspection apparatus may comprise rotating means for rotating the entity according to a predetermined rate profile having one or more periods of constant angular velocities, and/or for rotating the entity to another predetermined rate profile comprising rates of rotation causing the liquid to circulate and foreign bodies having densities higher than the liquid to accumulate at the container wall, and for bringing the container to a standstill, irradiating means, detection means, and electronic digital filtering comparison means.

Means of rotating the entity to be inspected comprise any means suitable for effecting either stepwise or continuous rotation. Presently a micro-processor controlled stepper motor stepping a predefined incremental angle of rotation synchronically with the scanning of the container is preferred. A preferred program comprises accelerating the entity to be inspected until a first constant rate of rotation at which the container and liquid are inspected for stationary parameters, said rate of rotation having a constant angular velocity. Depending on the scanning rate of the detection means and the required resolution, this inspection is performed at rotation rates generally below 2000 rpm, particularly below 1500 rpm, preferably about 1200 rpm. Further, the program comprises rotating, e.g. accelerating or decelerating, the entity to be inspected to a second, or optionally a third, a fourth, and so on, rate of rotation at which the container and liquid may be inspected for dynamic parameters, e.g. foreign bodies.

It is preferred that the rotation of the container is stopped prior to inspection for dynamic parameters of the liquid. Thus preferred rate profiles comprise intervals during which the liquid continues to circulate while the container is at rest. Accordingly, the micro-processor is programmed to decelerate the rotation of the container generally in less than 500 ms, particularly less than 100 ms, preferably in the range 20-80 ms. Accordingly, in a preferred embodiment, rotation means comprise a programmable stepper motor, preferably a low inertia stepper motor, programmed to provide a predefined rate profile over the total time of inspection and to stop the rotation generally in less than 500 ms, preferably in less than 100 ms, particularly in the range of 20-80 ms. In the case of suspensions or emulsions being inspected, it is generally preferred to shake or agitate the container prior to rotation, e.g. by rotating the container about an axis perpendicular to the axis of rotation, or by contacting the container with a vibrator.

In a preferred embodiment the transmitted or scattered radiation from the irradiated entity to be inspected is detected by detection means comprising an optical lens imaging the transmitted or scattered radiation, from preferably a narrow, e.g. 70 µm wide, vertical line segment of the container, onto a linear array of imaging photo detectors containing anywhere from 32 to 10000 elements, preferably a linear CCD- or PCCD-array having 1024 pixels of 10×10 µm, i.e. CCD-devices (charge coupled devices), or PCCD-devices (programmable charge coupled devices). Particularly preferred devices are linear CCD- or PCCD-arrays of high resolution. Further, the detection means comprise means for line scanning the pixels of the CCD-array serially, i.e. accessing the radiation sensitive elements sequentially, preferably every 200 µs, and by an analog video processing transforming an analog pixel value to a digital representation to be stored in a frame store memory or manipulated otherwise e.g. by digital filtering. In a preferred embodiment the detection means further comprises means for transforming the analog pixel value to a digital value. Color recognition may be applied via the use of color-CCD line-scanners having optical interference filters integrated directly on the line-scan CCD sensor chip. Therefore, in another preferred embodiment, three trigger controlled stroboscopic light sources are used each filtered for a red, green and blue output, and all feeding their output into the same fibre bundle guiding light to the container to be inspected. Three successive line-scans with respectively the red, green and blue sources illuminating the container facilitates a full colour image to be gathered, giving colour information on both the container and its contents.

In a preferred embodiment line scans are compared via comparison of actual or manipulated pixel values which comparison may be obtained by suitable electronic digital filtering and comparison means known per se. It is preferred that means of digital filtering comprises a digital matrix filter having filter coefficients loadable from software which matrix filter can be in the form of integrated circuits, or consist of conventional electronics comprising e.g. cascade shift registers, multipliers, subtractors, accumulators, etc. known to a person skilled in the art. Further, it is preferred that electronic comparison means comprises a frame store memory known per se which memory is computer controlled to store a complete unfolded image of the entity to be inspected, and the data of which may be processed by an image processing computer. In a preferred embodiment the electronic comparison means comprises a digital matrix filter and/or a frame store memory.

According to the present invention, distinction between dynamic parameters of the liquid and static parameters of the container wall can be provided by stopping the rotation of the entity to be inspected and scanning the entity while the liquid is still rotating at an almost unchanged predetermined rate. However, for entities to be inspected for stationary parameters only or entities having recognizable known dynamic parameters like trapped air bubbles of given sizes, stopping of the rotation of the container may be avoided.

In a preferred embodiment a "liquid-filled container" to be inspected may comprise any container that is transparent or semi-transparent to the electromagnetic radiation applied; particularly preferred transparent containers are cartridges, ampoules, vials, and capsules, produced from materials normally intended for containing pharmaceutical liquids, e.g. glass or plastic. Within the present context the expression "liquids" designates any liquids, mixtures, solutions, suspensions, colloidal dispersions, emulsions, etc., organic or inorganic; particularly pharmaceutical liquids comprising microsuspensions such as insulin. Further, within the present context the expression "inspection" designates the acts of inspecting an object for certain predefined quality assurance parameters for example in order to comply with rules of good manufacturing practice and warrants of products.

The test parameters for containers are not restricted to "presence of" or "absence of", but generally comprise a reproducible measurement that can be calculated from the unfolded image, the result being compared to the tolerance allowed for the particular test parameter, and subsequently used for an accept/reject decision. Similarly when inspecting labels, text recognition can be applied to ensure correct labelling. Contrary to prior art technique that applies different inspection means for inspection of stationary and dynamic parameters of liquid-filled containers, the present embodiment provides the possibility of applying a single line scanning apparatus for both classes of parameters. This possibility is surprisingly achieved through the combination of rotation schemes, according to the embodiment, and the line scanning apparatus providing for an unfolded image of the container and its contents.

According to a preferred embodiment, entities that have been inspected for one or more test parameters may be identified as unacceptable when a test parameter turns out to be outside the predefined range for acceptable values. Accordingly, in a preferred embodiment, the inspection apparatus further comprises means of identifying unacceptable entities. Thus identification of unacceptable entities can be based on the output signals of the digital filtering and comparison means, e.g. the output of the digital matrix filter or the output of the image processing computer having processed the data of the frame store memory. Further, in a preferred embodiment, the inspection apparatus comprises means for separating entities identified as unacceptable from approved entities. In one aspect of the invention such means of rejecting unacceptable entities comprises electronic and mechanical means of separating said unacceptable entities from accepted entities. When an entity is rejected the computer may store information about the type of parameter on the basis of which the rejection took place, thereby making it easier for the operator to identify the reason for a possible rise in the number of rejections.

In addition to the above described embodiments, any inspection methods and apparatuses that involves exposing a liquid-carrying container to electromagnetic irradiation and capturing at least one representation of at least one section of the container is within the scope of the present invention. Even though preferred, the container does not necessarily need to be rotated, the detection system does not necessarily need to be a line scanning system, etc., to obtain the advantages of the illumination method of the present invention. Also any means for capturing a representation is within the scope of the invention, e.g. a matrix camera capturing the whole width of a container at a time, or simply filming a rotating container or liquid with conventional digital camera means.

The invention claimed is:

1. Method of irradiating a liquid-carrying container for inspection, comprising
    rotating said container, its contents or both around a rotation axis and irradiating said container with an electromagnetic radiation beam from a first direction along an irradiation center plane substantially parallel to said rotation axis,
    wherein the irradiated cross-section of said container, irradiated by said electromagnetic radiation beam, has less width than the cross-section of said container, said irradiation center plane or its prolongation intersecting a detection center plane defined by a capturing device capturing from a second direction and being substantially parallel to said rotation axis, or its prolongation, in a line substantially parallel to said rotation axis and dislocated from said rotation axis in a direction opposite of said second direction, and avoiding illumination of said rotation axis.

2. Method of irradiating a liquid-carrying container according to claim 1, wherein a width of said irradiated cross-section is less than 10 mm.

3. Method of irradiating a liquid-carrying container according to claim 1, wherein said electromagnetic radiation beam comprises visible light.

4. Method of irradiating a liquid-carrying container according to claim 1, wherein said liquid is substantially opaque.

5. Method of irradiating a liquid-carrying container according to claim 1, wherein said liquid comprises a suspension.

6. Method of irradiating a liquid-carrying container according to claim 1, wherein said rotation is adapted to cause any of said content which has a density higher than the density of the main content to be pushed outwards against a container wall.

7. Method of irradiating a liquid-carrying container according to claim 1, wherein said liquid comprises an insulin micro-suspension.

8. Method of irradiating a liquid-carrying container according to claim 1, wherein said liquid is substantially transparent.

9. Method of irradiating a liquid-carrying container according to claim 1, wherein said liquid comprises a solution.

10. Method of irradiating a liquid-carrying container according to claim 1, wherein said rotation is adapted to cause any of said content which has a density lower than the density of the main content to be pulled inwards and assemble along said rotation axis.

11. Method of irradiating a liquid-carrying container according to claim 1, wherein said section that is captured is within said electromagnetic radiation beam or its prolongation.

12. Method of irradiating a liquid-carrying container according to claim 1, wherein the width of said irradiated cross-section corresponds approximately to the cross-section of said section as seen from the direction of said irradiation.

13. Irradiation system comprising
rotation means for rotating a liquid-carrying container, its contents or both around a rotation axis and
an illumination device for irradiating said container with an electromagnetic radiation beam from a first direction along an irradiation center plane substantially parallel to said rotation axis,
wherein said irradiation center plane or its prolongation intersects a detection center plane defined by a capturing device capturing from a second direction and being substantially parallel to said rotation axis, or its prolongation, in a line substantially parallel to said rotation axis and being located between said rotation axis and said capturing device, and said electromagnetic radiation beam being arranged so that illumination of said rotation axis is avoided.

14. Irradiation system according to claim 13, wherein said system further comprises a capturing device for capturing a representation of a section of said container.

15. Method for inspecting a liquid-carrying container for one or more test parameters of said container, the contents of said container, or both, the method comprising
rotating said container, said contents or both around a rotation axis,
irradiating said container with an electromagnetic radiation beam from a first direction along an irradiation center plane substantially parallel to said rotation axis,
capturing a representation of a section of said container from a second direction along a detection center plane substantially parallel to said rotation axis, and
processing said representation,
wherein the irradiated cross-section of said container, irradiated by said electromagnetic radiation beam, has less width than the cross-section of said container,
said irradiation center plane or its prolongation intersecting said detection center plane or its prolongation in a line substantially parallel to said rotation axis and dislocated from said rotation axis in a direction opposite of said second direction, and
avoiding illumination of said rotation axis.

16. Method for inspecting a liquid-carrying container according to claim 15, wherein the width of said electromagnetic radiation beam at the position where it enters said container is less than the width of said container as seen from said first direction.

17. Method for inspecting a liquid-carrying container according to claim 15, wherein said section is within said electromagnetic radiation beam or its prolongation.

18. Method for inspecting a liquid-carrying container according to claim 15, wherein a width of said electromagnetic radiation beam at the position where it enters said container is less than half the width of said container as seen from said first direction.

19. Method for inspecting a liquid-carrying container according to claim 15, wherein a width of said electromagnetic radiation beam at the position where it enters said container is less than 10 mm.

20. Method for inspecting a liquid-carrying container according to claim 15, wherein an angle between said irradiation center plane and said detection center plane is between 40 degrees and 140 degrees.

21. Method for inspecting a liquid-carrying container according to claim 15, wherein said electromagnetic radiation beam (46) comprises visible light.

22. Method for inspecting a liquid-carrying container according to claim 15, wherein said capturing a representation of a section of said container comprises performing a line scan parallel to said rotation axis.

23. Method for inspecting a liquid-carrying container according to claim 15, wherein said capturing a representation of a section of said container comprises taking a picture with a matrix camera.

24. Method for inspecting a liquid-carrying container according to claim 15, wherein said liquid is substantially opaque.

25. Method for inspecting a liquid-carrying container according to claim 15, wherein said liquid comprises a suspension.

26. Method for inspecting a liquid-carrying container according to claim 15, wherein said liquid comprises an insulin micro-suspension.

27. Method for inspecting a liquid-carrying container according to claim 15, wherein said liquid is substantially transparent.

28. Method for inspecting a liquid-carrying container according to claim 15, wherein said liquid comprises a solution.

29. Method for inspecting a liquid-carrying container according to claim 15, wherein said test parameters comprise existence of foreign bodies.

30. Method for inspecting a liquid-carrying container according to claim 15, wherein said processing comprises digital image processing.

31. Method for inspecting a liquid-carrying container according to claim 15, wherein said processing comprises analog signal processing.

32. Method for inspecting a liquid-carrying container according to claim 15, wherein said capturing a representation is repeated several times, and said step of processing said representation comprises comparing said representation with at least a part of at least one further representation of a section of said container.

33. Method for inspecting a liquid-carrying container for one or more test parameters of said container, the contents of said container, or both, comprising
  rotating said container, said contents or both around a rotation axis,
  irradiating said container with an electromagnetic radiation beam from a first direction along an irradiation center plane substantially parallel to said rotation axis,
  capturing a representation of a section of said container from a second direction along a detection center plane substantially parallel to said rotation axis, and
  processing said representation,
wherein a width of said electromagnetic radiation beam at the position where it enters said container is less than a width of said container as seen from said first direction, and wherein said irradiation center plane or its prolongation intersecting said detection center plane or its prolongation in a line substantially parallel to said rotation axis and dislocated from said rotation axis in a direction opposite of said second direction, and
avoiding illumination of said rotation axis.

34. Inspection system for liquid-carrying containers comprising
  rotation means for rotating a liquid-carrying container, its contents or both around a rotation axis,
  an illumination device for establishing an electromagnetic radiation beam for irradiating said container from a first direction along an irradiation center plane substantially parallel to said rotation axis,
  a capturing device for capturing a representation of a section of said container from a second direction along a detection center plane substantially parallel to said rotation axis, and
  processing means for processing said representation,
wherein said irradiation center plane or its prolongation intersects said detection center plane or its prolongation in a line substantially parallel to said rotation axis and being located between said rotation axis and said capturing device, and said electromagnetic radiation beam being arranged so that illumination of said rotation axis is avoided.

35. Inspection system according to claim 34, wherein said system comprises an irradiation system comprising rotation means for rotating a liquid-carrying container, its contents or both around a rotation axis and an illumination device for irradiating said container with an electromagnetic radiation beam, wherein the irradiated cross-section of said container, irradiated by said electromagnetic radiation beam, is less than the cross-section of said container.

36. Method of irradiating a liquid-carrying container according to claim 1, wherein said electromagnetic radiation beam is directed towards said section that is being captured in order to preferably illuminate that part of said liquid-carrying container only.

37. Irradiation system according to claim 13, wherein said electromagnetic radiation beam is directed towards said section that is being captured in order to preferably illuminate that part of said liquid-carrying container only.

38. Method for inspecting a liquid-carrying container according to claim 15, wherein said electromagnetic radiation beam is directed towards said section that is being captured in order to preferably illuminate that part of said liquid-carrying container only.

39. Inspection system according to claim 34, wherein said electromagnetic radiation beam is directed towards said section that is being captured in order to preferably illuminate that part of said liquid-carrying container only.

* * * * *